United States Patent [19]
Abe et al.

[11] Patent Number: 5,508,385
[45] Date of Patent: Apr. 16, 1996

[54] TRIPEPTIDE DERIVATIVES CONTAINING PYROGLUTAMIC ACID RESIDUE

[75] Inventors: Yoshihito Abe, Koriyama; Takeshi Nagasawa, Urawa; Katsumasa Kuroiwa; Katsuhiro Yaginuma, both of Koriyama, all of Japan

[73] Assignee: Nitto Boseki Co., Ltd., Fukushima, Japan

[21] Appl. No.: 746,472

[22] Filed: Aug. 16, 1991

[30] Foreign Application Priority Data

Sep. 5, 1990 [JP] Japan ................................. 2-235109

[51] Int. Cl.$^6$ .............................. A61K 38/00; C07K 5/08; C07K 5/00
[52] U.S. Cl. .............................................. 530/331
[58] Field of Search ............................... 514/18; 530/331

[56] References Cited

U.S. PATENT DOCUMENTS 4,401,594  8/1983  Umezawa et al. .
5,116,941  5/1992  Nakatsuyama et al. ............... 530/331

OTHER PUBLICATIONS

Chemical Abstracts, vol. 115 (13), 126794n.
Aoyagi et al., J. Antibiotics (Tokyo) 22:283–286 (1969).
Taisha, vol. 14, pp. 1087–1098 (1977).
Bajusz, Symposia Biologica Hungarica 25:277–298 (1984).
Saino et al., J. Antibiotics, 41:220–225 (1988).

*Primary Examiner*—Christina Y. Chan
*Assistant Examiner*—S. G. Marshall
*Attorney, Agent, or Firm*—Darby & Darby

[57] ABSTRACT

Novel tripeptide derivatives having a pyroglutamic acid residue strongly inhibit a plurality of trypsin-like serine proteases such as plasmin, thrombin, trypsin, kallikrein, factor Xa and urokinase. The compounds of the present invention can inhibit various trypsin-like serine proteases and are expected to show remarkable effects as novel protease inhibitors for the treatment of pancreatitis, inflammantion, ulcer, etc.

2 Claims, No Drawings

TRIPEPTIDE DERIVATIVES CONTAINING PYROGLUTAMIC ACID RESIDUE

BACKGROUND OF THE INVENTION

1. Field of the Invention

The present invention relates to novel tripeptide derivatives containing a pyroglutamic acid residue and more particularly, to tripeptide derivatives containing a pyroglutamic acid residue which possess a protease inhibitory activity, or pharmaceutically acceptable salts thereof. The invention also relates to protease inhibitors comprising the same as an effective ingredient.

2. Related Art Statement

It is well known that a variety of proteases are present in vivo. There are known trypsin-like enzymes, for example, plasmin, trypsin, kallikrein, thrombin, urokinase, etc., or chymotrypsin-like enzymes, pepsin-like enzymes, or the like. It is known that these proteases cause various diseases when they are abnormally activated by some reason.

Accordingly, a substance having an inhibitory activity against these proteases is useful as a certain therapeutic agent in the clinical field. For example, an anti-plasmin agent is useful as a hemostatic, anti-inflammatory agent or anti-allergic agent; an anti-thrombin agent is useful for the treatment of thrombosis; an anti-trypsin agent is useful for the treatment of pancreatitis; an anti-kallikrein agent is useful for the treatment of inflammation and ulcer; and an anti-urokinase agent is useful for preventing hemorrhagic conditions in thrombolytic therapy with urokinase.

Protease inhibitors having such activities have been heretofore developed but they have merely poor protease inhibitory activities and are insufficient to provide as drugs for practical use. Protease inhibitors having a sufficient inhibitory activity against a plurality of proteases has not been yet developed, either.

For example, certain tripeptide derivatives containing an argininal group are widely known. That is, acetyl-L-leucyl-L-leucyl-L-argininal (leupeptin) is one of the argininal-containing tripeptide derivatives produced by a certain kind of microorganism (cf., e.g., J. Antibiotics (Tokyo), 1969, 22, 283) but its inhibitory activity is poor (cf., e.g., Taisha, 1977, 14, 1087). D-Phenylalanyl-L-propyl-L-argininal is known to be a thrombin inhibitor (see, e.g., Symposia Biologica Hungarica, 1984, 25, 277) but its inhibitory activity against other similar trypsin-like enzymes is weak. Umezawa et al. synthesized many derivatives of leupeptin but any of them merely shows a weak inhibitory activity against trypsin-like enzymes (cf., J. Antibiotics (Tokyo), 1988, 41 (2), 220).

SUMMARY OF THE INVENTION

An object of the present invention is to dissolve the foregoing problems in the prior art, and to develop compounds having a sufficient inhibitory activity for practical use and a sufficient inhibitory activity against a plurality of proteases and to obtain protease inhibitors comprising the same as an effective ingredient.

The present inventor has made extensive investigations on survey of compounds having a more potent and broader inhibitory activity than conventional protease inhibitors. As a result, it has been found that tripeptide derivatives having an amino acid sequence of L- or D-pyroglutamic acid or L- or D-pyroglutamic acid having a certain functional group at its N-terminus; then glycine, L-alanine, L-valine, L-leucine (with proviso that the D-pyroglutamic acid residue follows), L-isoleucine, L-serine, L-threonine, L-lysine, L-proline, L-pipecoline or L-phenylalanine; and then L-, D- or DL-argininal, or their acid addition salts exert on an excellent protease inhibitory activity. The present invention has thus been completed.

That is, the feature of the present invention lies in tripeptide derivatives represented by the following general formula (I):

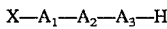  (I)

wherein X represents hydrogen atom, an arenesulfonyl group (including the one containing an alkyl group or an alkyloxy group as a substituent), an alkanesulfonyl group (including the one containing an aryl group as a substituent) group, an aroyl group (including the one containing an alkyl group, a halogen atom, an amine derivative group or an alkyloxy group as a substituent), an acyl group (including the one containing an aryl group as a substituent), or an alkyloxycarbonyl group (including the one containing an aryl group as a substituent), which is bound to the secondary amino group of $A_1$; $A_1$ represents L- or D-pyroglutamic acid residue bound to the primary amino group of $A_2$; $A_2$ represents glycine residue, L-alanine residue, L-valine residue, L-leucine residue (with proviso that $A_1$ is D-pyroglutamic acid residue), L-isoleucine residue, L-serine residue, L-threonine residue, L-lysine residue, L-proline residue, L-pipecolinic acid residue or L-phenylalanine residue, which is bound to the primary amino group of $A_3$; and $A_3$ represents L-, D- or DL-arginine residue; or pharmaceutically acceptable acid addition salts thereof; and protease inhibitors comprising the tripeptide derivatives or their acid addition salts as an effective ingredient. The compounds of the present invention described above strongly inhibit various proteases.

X in formula (I) is a substituent on the secondary amino group in the L- or D-pyroglutamic acid residue of $A_1$. Preferred examples of the arenesulfonyl group shown by X include benzenesulfonyl or naphthalenesulfonyl; a $C_{1-6}$-alkyl-substituted benzenesulfonyl group or a $C_{1-6}$-alkyl-substituted naphthalenesulfonyl group such as p-toluenesulfonyl, mesitylenesulfonyl, etc.; a $C_{1-6}$-alkyloxy-substituted benzenesulfonyl group or a $C_{1-6}$-alkyloxy-substituted naphthalenesulfonyl group such as p-methoxybenzenesulfonyl, etc.

Preferred examples of the alkanesulfonyl group include a $C_{1-6}$-alkanesulfonyl group such as methanesulfonyl, ethanesulfonyl, propanesulfonyl, butanesulfonyl, etc.; or a phenyl-substituted $C_{1-6}$-alkanesulfonyl group such as phenylmethanesulfonyl, etc.

Preferred examples of the aroyl group include benzoyl or naphthoyl; a $C_{1-6}$-alkyl-substituted benzoyl group or a $C_{1-6}$-alkyl-substituted naphthoyl group such as toluoyl, p-ethylbenzoyl, etc.; a halogen-substituted benzoyl group or a halogen-substituted naphthoyl group such as p-chlorobenzoyl, etc.; an amino-$C_{1-6}$-alkyl-substituted benzoyl group or a $C_{1-6}$-alkyl-substituted naphthoyl group such as p-aminomethylbenzoyl, etc.; a $C_{1-6}$-alkyloxy-substituted benzoyl group or a $C_{1-6}$-alkyloxy-substituted naphthoyl group such as p-methoxybenzoyl, p-ethoxybenzoyl, etc.

Preferred examples of the acyl group include a $C_{2-10}$-acyl group such as acetyl, propionyl, octanoyl, etc.; a phenyl-substituted $C_{2-10}$-acyl group such as phenylacetyl, etc.

Preferred examples of the alkyloxycarbonyl group include a $C_{1-6}$-alkyloxycarbonyl group such as methoxycarbonyl, ethoxycarbonyl, propoxycarbonyl, butoxycarbonyl, pentoxycarbonyl, hexoxycarbonyl, etc.; or a phenyl-substituted $C_{1-6}$-alkyloxycarbonyl group such as benzyloxycarbonyl, etc.

3

Preferred examples of X include hydrogen atom and a phenyl-substituted $C_{1-6}$-alkyloxycarbonyl group such as benzyloxycarbonyl, etc.

As $A_1$ in formula (I), L-pyroglutamic acid residue is particularly preferred; L-proline residue, L-alanine residue, L-phenylalanine residue and L-leucine residue are particularly preferred as $A_2$; and L-arginine residue is particularly preferred as $A_3$.

The compounds of the present invention and pharmaceutically acceptable acid addition salts thereof may be prepared by various processes. Taking as an example the case where subtituent X in general formula (I) is benzyloxycarbonyl and the acid addition salt is the hydrochloride or sulfate, the processes are described below. However, preparation of the tripeptide derivatives of the present invention and acid addition salts thereof are not deemed to be limited only to these processes.

The hydrochloride and sulfate of the tripeptide derivative of formula (I) wherein X is hydrogen or benzyloxycarbonyl (Z) group can be synthesized according to the processes shown by the following reaction schemes 1) to 5).

Reaction Scheme

1) Z—L—pGlu—A$_2$—L—Arg—H.HCl (I')

Z—L—pGlu—A$_2$—OSu +

H—L—Arg—H.(OBu)$_2$.HCl ——→
(III)

Z—L—pGlu—A$_2$—L—Arg—H.(OBu)$_2$.HCl $\xrightarrow{H^+}$
(II)

Z—L—pGlu—A$_2$—L—Arg—H.HCl
(I')

2) Z—L—pGlu—A$_2$—L—Arg—H.HCl (I')

Z—A$_2$—OSu + H—L—Arg—H.(OBu)$_2$.HCl ——→
(III)

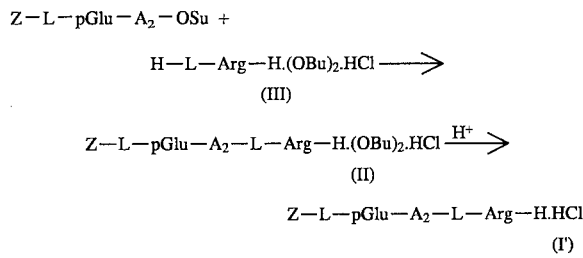

3) H—L—pGlu—A$_2$—L—Arg—H.HCl (I")

Z—L—pGlu—A$_2$—L—Arg—H.HCl $\xrightarrow{H_2}$
(I')

H—L—pGlu—A$_2$—L—Arg—H.HCl
(I")

4) Z—L—pGlu—A$_2$—L—Arg—H.½H$_2$SO$_4$ (I''')

-continued
Reaction Scheme

Z—L—pGlu—A$_2$—L—Arg—H.(OBu)$_2$.HCl $\xrightarrow{H_2SO_4/Na_2SO_4}$
(II)

Z—L—pGlu—A$_2$—L—Arg—H.(OBu)$_2$.½H$_2$SO$_4$ $\xrightarrow{H^+}$
(VI)

Z—L—pGlu—A$_2$—L—Arg—H.½H$_2$SO$_4$
(I''')

5) H—L—pGlu—A$_2$—L—Arg—H.½H$_2$SO$_4$ (I'''')

Z—L—pGlu—A$_2$—L—Arg—H.½H$_2$SO$_4$ $\xrightarrow{H_2}$
(I''')

H—L—pGlu—A$_2$—L—Arg—H.½H$_2$SO$_4$
(I'''')

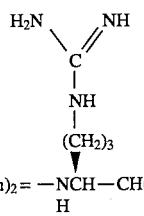

Arg—H.(OBu)$_2$ = —NCH—CH(OBu)$_2$
            H

Z = benzyloxycarbonyl

OSu = N-hydroxysuccinimide ester

Based on the reaction schemes described above, the processes for synthesis are described below.

1) The N-benzyloxycarbonyl-L-pyroglutamyl-A$_2$-L-argininal hydrochloride (I') may be obtained by hydrolysis of the corresponding N-benzyloxycarbonyl-L-pyroglutamyl-A$_2$-L-argininal dibutylacetal hydrochloride (II) in diluted hydrochloric acid aqueous solution-acetonitrile.

Compound (II) can be prepared according to conventional process for synthesizing peptide using L-argininal dibutylacetal hydrochloride (III) (cf. Japanese Patent Application KOKAI No. 1-8963) as a starting material (cf., e.g., Nobuo Izumiya et al., "Basis and Experiment of Peptide Synthesis", Maruzen Publishing Co.). For example, Compound (II) may be obtained by condensation of Compound (III) and an activated ester (e.g., N-hydroxysuccinimide ester) of N-benzyloxycarbonyl-L-pyroglutamyl-A$_2$-OH in a suitable solvent (e.g., methylene chloride).

2) Compound (II) may also be synthesized as follows. The desired Compound (II) may be obtained by condensing Compound (III) with an activated ester (e.g., N-hydroxysuccinimide ester) of Z—A$_2$—OH in a suitable solvent (e.g., methanol) to give N-benzyloxycarbonyl-A$_2$-L-argininal dibutylacetal hydrochloride (IV), catalytically hydrogenating Compound (IV) in a suitable solvent (e.g., methanol) in the presence of a catalyst (e.g., palladium black) to give H-A$_2$-L-argininal dibutylacetal (V), and condensing Compound (V) with an activated ester (e.g., N-hydroxysuccinimide ester) of benzyloxycarbonyl-L-pyroglutamic acid in a suitable solvent (e.g., methylene chloride).

3) L-Pyroglutamyl-A$_2$-L-argininal hydrochloride (II') may be obtained by catalytically hydrogenating the corresponding N-benzyloxycarbonyl-L-pyroglutamyl-A$_2$-L-argininal hydrochloride (I') in a suitable solvent (e.g., methanol) in the presence of a catalyst (e.g., palladium black).

4) N-Benzyloxycarbonyl-L-pyroglutamyl-A$_2$-L-argininal ½ sulfate (I''') may be obtained by dissolving N-benzyloxycarbonyl-L-pyroglutamyl-A$_2$-L-argininal dibutylacetal hydrochloride (II) in chloroform and washing the solution with saturated sodium sulfate aqueous solution containing 5% sulfuric acid to obtain N-benzyloxycarbonyl-L-pyroglutamyl-$A_2$-L-argininal dibutylacetal sulfate (VI), and hydrolyzing Compound (VI) with a solvent mixture of diluted sulfuric acid and acetonitrile.

5) L-Pyroglutamyl-$A_2$-L-argininal ½ sulfate (I"") may be obtained by catalytically hydrogenating N-benzyloxycarbonyl-L-pyroglutamyl-$A_2$-L-argininal ½ sulfate (I''') in a suitable solvent (e.g., aqueous methanol) in the presence of a catalyst (e.g., palladium black).

Also in the case that substituent X represents not only benzyloxycarbonyl but also an arenesulfonyl (including the one containing an alkyl group or an alkyloxy group as a substituent), an alkanesulfonyl group (including the one containing an aryl group as a substituent) group, an aroyl group (including the one containing an alkyl group, a halogen atom, an amine derivative group or an alkyloxy group as a substituent), an acyl group (including the one containing an aryl group as a substituent), or an alkyloxycarbonyl group (including the one containing an aryl group as a substituent), the tripeptide derivatives and their acid addition salts may be synthesized by process similar to 1), 2) or 4) shown above.

Also where the pyroglutamic acid residue of $A_1$ takes D-configuration or where the arginine residue of $A_3$ takes D- or DL-configuration, the processes for synthesis described above similarly apply to give the compounds of the present invention.

In the processes described above, the final products of the tripeptide derivatives may contain a very small amount of the products having D-configurations of L-argininal parts.

The acid addition salts of the tripeptide derivatives of general formula (I) can be used as drugs for therapeutic purposes, like the tripeptide derivatives and are advantageously acceptable pharmacologically and pharmaceutically. However, the basis for the activity resides in the tripeptide derivative per se which is the basic moiety but the acid moiety is not so important. However, difference in acid results in easy isolation or stability of compound and difference in solubility. Examples of suitable acid addition salts of the tripeptide derivatives of general formula (I) are inorganic acids such as hydrochlorides, hydrobromides, sulfates, etc.; organic carboxylates such as acetates, oxalates, succinates, maleates, citrates, lactates, etc.; organic sulfonates such as benzenesulfonates, p-toluenesulfonates, methanesulfonates, etc. Salts which are difficultly acceptable (e.g., hydrofluoride and perchlorate) or pharmaceutically unacceptable may also be utilized for isolation of the pharmaceutically acceptable salts or for purification of the base; or, they are useful and valuable for preparing the pharmaceutically acceptable salts by methods well known to one skilled in the art. Where the tripeptide derivatives have a plurality of free amino groups, the tripeptide derivatives may be used in the form of mono- or polyacid addition salts or in the form of mixed acid addition salts of a plurality of acids.

It has been confirmed that the tripeptide derivatives of the present invention and their acid addition salts all exhibit a highly inhibitory activity against each enzyme, when the activity of protease is measured in the presence of a trypsin-like serine protease such as plasmin, thrombin, trypsin, kallikrein, factor $X_a$, urokinase, etc.

Therefore, the protease inhibitor comprising as an effective ingredient the tripeptide derivative represented by general formula (I) or pharmaceutically acceptable acid addition salts thereof is effective for the treatment of trypsin-like serine protease-associated diseases, for example, inflammation, hemorrhage, allergy, pancreatitis or ulcer.

In the case of using the compound of the present invention as a drug, method for administration is not necessarily limited. The compound is prepared into a suitable pharmaceutical by conventional pharmaceutical methods and administered by intravenous injection, intramuscular injection, intravenous drop, oral administration, etc. A suitable daily dose is 1 mg to 1000 mg per adult but needless to say, may be varied appropriately, if necessary and desired.

EXAMPLES

Hereafter the present invention is described by reference to specific examples, wherein the following abbreviations are used.

M=molar concentration
N=normal concentration
g=gram
mg=milligram
ml=milliliter
mmol=millimolar amount
mp=melting point
dec=decomposed
mM=millimolar concentration
Rf=relative movility in thin layer chromatography
DMF=dimethylformamide
CHA=3-carboxy-4-hydroxyanilide
PNA=p-nitroanilide
MS=mass spectrum
m/z=mass/number of electric charge
$MH^+$=(molecular weight+1)
pH=potential of hydrogen In TLC, silica gel $F_{254}$ (made by Merck) plate was used and the following solvents were used.

$Rf_1$=chloroform:methanol:acetic acid:water (40:10:1:1)
$Rf_2$=1-butanol:acetic acid:water (4:1:1)
$Rf_3$=1-butanol:n-butyl acetate:acetic acid:water (2:1:1:1)
$Rf_4$=chloroform:methanol:acetic acid (40:10:5)
$Rf_5$=ethyl acetate:pyridine:acetic acid:water (30:20:6:11)

Example 1

Synthesis of
N-benzyloxycarbonyl-L-pyroglutamyl-L-prolyl-L-argininal hydrochloride a) N-Benzyloxycarbonyl-L-pyroglutamyl-L-prolyl-L-argininal dibutylacetal hydrochloride To a suspension of L-argininal dibutylacetal hydrochloride (0.65 g, 2.0 ml, cf. Japanese Patent Application KOKAI No. 1-8963) in methylene chloride (20 ml) were added triethylamine (0.28 ml, 2.0 mmols) and then N-benzyloxycarbonyl-L-pyroglutamyl-L-proline-N-hydroxysuccinimide ester (1.07 g, 2.4 mmols) at room temperature. The reaction mixture was stirred overnight at room temperature. After completion of the reaction, the reaction mixture was washed with saturated sodium chloride aqueous solution and concentrated. The residue (1.32 g) was subjected to silica gel column chromatography and eluted with chloroform:methanol:acetic acid (90:10:5, and then 50:10:5) to give 0.91 g (68%) of N-benzyloxycarbonyl-L-pyroglutamyl-L-prolyl-L-argininal dibutylacetal hydrochloride as oil.

TLC: $Rf_1$=0.27–0.36 b) N-Benzyloxycarbonyl-L-pyroglutamyl-L-prolyl-L-argininal hydrochloride

After 1N hydrochloric acid aqueous solution (30 ml) was added to a solution of N-benzyloxycarbonyl-L-pyroglutamyl-L-prolyl-L-argininal dibutylacetal hydrochloride (0.40 g, 0.60 mmol) in acetonitrile (60 ml), the mixture was reacted at 36° C. for an hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 0.26 g (80%) of N-benzyloxycarbonyl-L-pyroglutamyl-L-prolyl-L-argininal hydrochloride.

mp=85° C. (dec.)
$Rf_2$=0.13–0.33
$[\alpha]_D^{20}$=−48° (c=0.1, DMF)

| Elemental analysis (as $C_{24}H_{33}N_6O_6Cl \cdot H_2O$) | | | |
|---|---|---|---|
| | C | H | N |
| Calcd. (%) | 51.94 | 6.36 | 15.14 |
| Found (%) | 51.54 | 6.16 | 14.98 |

Example 2

Synthesis of N-benzyloxycarbonyl-L-pyroglutamyl-L-alanyl-L-argininal hydrochloride a) N-Benzyloxycarbonyl-L-alanyl-L-argininal dibutylacetal hydrochloride

N-Benzyloxycarbonyl-L-alanine-N-hydroxysuccinimide ester (0.53 g, 1.65 mmol) was used instead of N-benzyloxycarbonyl-L-pyroglutamyl-L-proline-N-hydroxysuccinimide ester and, a suspension of L-argininal dibutylacetal hydrochloride (0.49 g, 1.50 mmol) in methylene chloride (15 ml) and triethylamine (0.21 ml, 1.50 mmol) were reacted therewith in a manner similar to Example 1 a) to give 0.48 g (80%) of N-benzyloxycarbonyl-L-alanyl-L-argininal dibutylacetal hydrochloride as oil.

TLC: $Rf_1$=0.34–0.41 b) L-Alanyl-L-argininal dibutylacetal hydrochloride

After N-benzyloxycarbonyl-L-alanyl-L-argininal dibutylacetal hydrochloride (0.45 g, 0.85 mmol) was dissolved in methanol (25 ml), palladium black (1 g) was added to the solution. The mixture was stirred at room temperature for 2 hours in a hydrogen flow. After completion of the reaction, the catalyst was filtered off and the filtrate was concentrated to give 0.33 g (97%) of L-alanyl-L-argininal dibutylacetal hydrochloride as oil.

TLC: $Rf_3$=0.43–0.54 c) N-Benzyloxycarbonyl-L-pyroglutamyl-L-alanyl-L-argininal dibutylacetal hydrochloride To a solution of L-alanyl-L-argininal dibutylacetal hydrochloride (0.32 g, 0.80 mmol) in methylene chloride (8 ml) were added triethylamine (0.11 ml, 0.80 mmol) and then N-benzyloxycarbonyl-L-pyroglutamic acid-N-hydroxysuccinimide ester (0.32 g, 0.88 mmol) at room temperature. The reaction mixture was stirred overnight at room temperature. After completion of the reaction, the reaction mixture was washed with saturated sodium chloride aqueous solution and concentrated. The residue (0.47 g) was subjected to silica gel column chromatography and eluted with chloroform:methanol:acetic acid (70:10:5) to give 0.24 g (47%) of N-benzyloxycarbonyl-L-pyroglutamyl-L-alanyl-L-argininal dibutylacetal hydrochloride as oil.

TLC: $Rf_1$=0.28–0.38 d) N-Benzyloxycarbonyl-L-pyroglutamyl-L-alanyl-L-argininal hydrochloride

To a solution of N-benzyloxycarbonyl-L-pyroglutamyl-L-alanyl-L-argininal dibutylacetal hydrochloride (0.22 g, 0.35 mmol) in acetonitrile (35 ml) was added 1N hydrochloric acid aqueous solution (17.5 ml). The mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform-methanol (20:1) was added to the residue. Insoluble matters were removed by filtration. After the filtrate was concentrated, the residue was recrystallized from chloroform-hexane to give 0.10 g (57%) of N-benzyloxycarbonyl-L-pyroglutamyl-L-alanyl-L-argininal hydrochloride.

TLC: $Rf_2$=0.36–0.55
mp=105° C. (dec.)
$[\alpha]_D^{20}$=−20° (c=0.5, DMF)

| Elemental analysis (as $C_{20}H_{31}N_6O_6Cl \cdot 2H_2O$) | | | |
|---|---|---|---|
| | C | H | N |
| Calcd. (%) | 48.31 | 6.45 | 15.36 |
| Found (%) | 48.70 | 6.14 | 14.95 |

Example 3

Synthesis of N-benzyloxycarbonyl-L-pyroglutamyl-L-phenylalanyl-L-argininal hydrochloride a) N-Benzyloxycarbonyl-L-phenylalanyl-L-argininal dibutylacetal hydrochloride N-Benzyloxycarbonyl-L-phenylalanine-N-hydroxysuccinimide ester (1.31 g, 3.3 mmols) was used instead of N-benzyloxycarbonyl-L-pyroglutamyl-L-proline-N-hydroxysuccinimide ester and, a suspension of L-argininal dibutylacetal hydrochloride (0.98 g, 3.0 mmols) in methylene chloride (30 ml) and triethylamine (0.42 ml, 3.0 mmols) were reacted therewith in a manner similar to Example 1 a) to give 1.31 g (72%) of N-benzyloxycarbonyl-L-phenylalanyl-L-argininal dibutylacetal hydrochloride as oil.

TLC: $Rf_1$=0.47–0.55 b) L-Phenylalanyl-L-argininal dibutylacetal hydrochloride

After N-benzyloxycarbonyl-L-phenylalanyl-L-argininal dibutylacetal hydrochloride (1.24 g, 2.05 mmols) was dissolved in methanol (100 ml), palladium black (1 g) was added to the solution. The mixture was stirred at room temperature for 2 hours in a hydrogen flow. After completion of the reaction, the catalyst was filtered off and the filtrate was concentrated to give 0.93 g (96%) of L-phenylalanyl-L-argininal dibutylacetal hydrochloride as oil.

TLC: $Rf_3$=0.52–0.58 c) N-Benzyloxycarbonyl-L-pyroglutamyl-L-phenylalanyl-L-argininal dibutylacetal hydrochloride To a solution of L-phenylalanyl-L-argininal dibutylacetal hydrochloride (0.45 g, 0.95 mmol) in methylene chloride (9.5 ml) were added triethylamine (0.13 ml, 0.95 mmol) and then N-benzyloxycarbonyl-L-pyroglutamic acid-N-hydroxysuccinimide ester (0.38 g, 1.05 mmol) at room temperature. The reaction mixture was stirred overnight at room temperature. After completion of the reaction, the reaction mixture was washed with saturated sodium chloride aqueous solution and concentrated. The residue (0.64 g) was subjected to silica gel column chromatography and eluted with chloroform:methanol:acetic acid (100:10:5 and then 70:10:5) to give 0.37 g (55%) of N-benzyloxycarbonyl-L-pyroglutamyl-L-phenylalanyl-L-argininal dibutylacetal hydrochloride as oil.

TLC: $Rf_1$=0.27–0.31 d) N-Benzyloxycarbonyl-L-pyroglutamyl-L-phenylalanyl-L-argininal hydrochloride

To a solution of N-benzyloxycarbonyl-L-pyroglutamyl-L-phenylalanyl-L-argininal dibutylacetal hydrochloride (72 mg, 0.10 mmol) in acetonitrile (10 ml) was added 1N hydrochloric acid aqueous solution (5 ml). The mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 36 mg (61%) of N-benzyloxycarbonyl-L-pyroglutamyl-L-phenylalanyl-L-argininal hydrochloride.

TLC: $Rf_2$=0.31–0.45 mp=90° C. (dec.)

MS: m/z 553 (MH$^+$)

Example 4

Synthesis of N-benzyloxycarbonyl-L-pyroglutamyl-glycyl-L-argininal hydrochloride a) N-Benzyloxycarbonyl-glycyl-L-argininal dibutylacetal hydrochloride N-Benzyloxycarbonyl-glycine-N-hydroxysuccinimide ester (1.29 g, 4.20 mmols) was used instead of N-benzyloxycarbonyl-L-pyroglutamyl-L-proline-N-hydroxysuccinimide ester and, a suspension of L-argininal dibutylacetal hydrochloride (1.14 g, 3.50 mmols) in methylene chloride (35 ml) and triethylamine (0.49 ml, 3.50 mmols) were reacted therewith in a manner similar to Example 1 a) to give 1.69 g (93%) of N-benzyloxycarbonyl-glycyl-L-argininal dibutylacetal hydrochloride as oil.

TLC: $Rf_4$=0.37–0.48 b) Glycyl-L-argininal dibutylacetal hydrochloride

After N-benzyloxycarbonyl-glycyl-L-argininal dibutylacetal hydrochloride (1.60 g, 3.10 mmols) was dissolved in methanol (250 ml), palladium black (1 g) was added to the solution. The mixture was stirred at room temperature for 2 hours in a hydrogen flow. After completion of the reaction, the catalyst was filtered off and the filtrate was concentrated to give 1.20 g (100%) of glycyl-L-argininal dibutylacetal hydrochloride as oil.

TLC: $Rf_3$=0.24–0.41 c) N-Benzyloxycarbonyl-L-pyroglutamyl-glycyl-L-argininal dibutylacetal hydrochloride To a solution of glycyl-L-argininal dibutylacetal hydrochloride (0.12 g, 0.30 mmol) in methylene chloride (3 ml) were added triethylamine (0.042 ml, 0.30 mmol) and then N-benzyloxycarbonyl-L-pyroglutamic acid-N-hydroxysuccinimide ester (0.11 g, 0.36 mmol) at room temperature. The reaction mixture was stirred overnight at room temperature. After completion of the reaction, the reaction mixture was washed with saturated sodium chloride aqueous solution and concentrated. The residue (0.15 g) was purified by centrifugal liquid-liquid partition chromatography (Sanki Engineering Co., butanol-water, descending method) to give 0.03 g (16%) of N-benzyloxycarbonyl-L-pyroglutamyl-glycyl-L-argininal dibutylacetal hydrochloride as oil.

TLC: $Rf_1$=0.17–0.22 d) N-Benzyloxycarbonyl-L-pyroglutamyl-glycyl-L-argininal hydrochloride

To a solution of N-benzyloxycarbonyl-L-pyroglutamyl-glycyl-L-argininal dibutylacetal hydrochloride (30 mg, 0.048 mmol) in acetonitrile (4.8 ml) was added 1N hydrochloric acid aqueous solution (2.4 ml). The mixture was reacted at 36° C. for an hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 15.7 mg (66%) of N-benzyloxycarbonyl-L-pyroglutamyl-glycyl-L-argininal hydrochloride.

TLC: $Rf_2$=0.21–0.34 mp=85° C. (dec.)

MS: m/z 461 (MH$^+$)

Example 5

Synthesis of N-benzyloxycarbonyl-L-pyroglutamyl-L-pipecolyl-L-argininal hydrochloride a) N-Benzyloxycarbonyl-L-pyroglutamyl-L-pipecolyl-L-argininal dibutylacetal hydrochloride To a suspension of L-argininal dibutylacetal hydrochloride (0.16 g, 0.50 mmol) in methylene chloride (5 ml) were added triethylamine (0.07 ml, 0.5 mmol) and then N-benzyloxycarbonyl-L-pyroglutamyl-L-pipecolyl-N-hydroxysuccinimide ester (0.26 g, 0.55 mmol) at room temperature. The reaction mixture was stirred overnight at room temperature. After completion of the reaction, the reaction mixture was washed with saturated sodium chloride aqueous solution and concentrated. The residue (0.24 g) was subjected to silica gel (12 g) column chromatography and eluted with chloroform:methanol:acetic acid (90:10:5, and then 70:10:5) to give 0.15 g (43%) of N-benzyloxycarbonyl-L-pyroglutamyl-L-pipecolyl-L-argininal dibutylacetal hydrochloride as oil.

TLC: $Rf_1$=0.30–0.36 b) N-Benzyloxycarbonyl-L-pyroglutamyl-L-pipecolyl-L-argininal hydrochloride

After 1N hydrochloric acid aqueous solution (2.5 ml) was added to a solution of N-benzyloxycarbonyl-L-pyroglutamyl-L-pipecolyl-L-argininal dibutylacetal hydrochloride (35 mg, 0.05 mmol) in acetonitrile (5 ml), the mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 21 mg (76%) of N-benzyloxycarbonyl-L-pyroglutamyl-L-pipecolyl-L-argininal hydrochloride.

TLC: $Rf_2$=0.36–0.53

MS: m/z 515 (MH$^+$)

Example 6

Synthesis of N-benzyloxycarbonyl-D-pyroglutamyl-L-prolyl-L-argininal hydrochloride a) N-Benzyloxycarbonyl-D-pyroglutamyl-L-prolyl-L-argininal dibutylacetal hydrochloride To a suspension of L-argininal dibutylacetal hydrochloride (0.65 g, 2.0 mmols) in methylene chloride (20 ml) were added triethylamine (0.28 ml, 2.0 mmols) and then N-benzyloxycarbonyl-D-pyroglutamyl-L-proline-N-hydroxysuccinimide ester (1.07 g, 2.4 mmols) at room temperature. The reaction mixture was stirred overnight at room temperature. After completion of the reaction, the reaction mixture was washed with saturated sodium chloride aqueous solution and concentrated. The residue (1.32 g) was subjected to silica gel (66 g) column chromatography and eluted with chloroform:methanol:acetic acid (90:10:5, and then 50:10:5) to give 0.81 g (61%) of N-benzyloxycarbonyl-D-pyroglutamyl-L-prolyl-L-argininal dibutylacetal hydrochloride as oil.

TLC: $Rf_1$=0.31–0.37 b) N-Benzyloxycarbonyl-D-pyroglutamyl-L-prolyl-L-argininal hydrochloride

After 1N hydrochloric acid aqueous solution (30 ml) was added to a solution of N-benzyloxycarbonyl-D-pyroglutamyl-L-prolyl-L-argininal dibutylacetal hydrochloride (0.40 g, 0.60 mmol) in acetonitrile (60 ml), the mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 0.33 g (100%) of N-benzyloxycarbonyl-D-pyroglutamyl-L-prolyl-L-argininal hydrochloride.

TLC: $Rf_2$=0.19–0.32 mp=85° C. (dec.)

$[\alpha]_D^{20}$=−40° (c=0.5, DMF)

| Elemental analysis (as $C_{24}H_{33}N_6O_6Cl$ 3/2$H_2O$.2/5NaCl) | | | |
|---|---|---|---|
| | C | H | N |
| Calcd. (%) | 49.07 | 6.18 | 14.30 |
| Found (%) | 49.50 | 6.08 | 13.74 |

Example 7

Synthesis of N-benzyloxycarbonyl-D-pyroglutamyl-L-leucyl-L-argininal hydrochloride a) N-Benzyloxycarbonyl-L-leucyl-L-argininal dibutylacetal hydrochloride

N-Benzyloxycarbonyl-L-leucyl-N-hydroxysuccinimide ester (0.32 g, 2.3 mmols) was used instead of N-benzyloxycarbonyl-L-pyroglutamyl-L-prolyl-N-hydroxysuccinimide ester and, a suspension of L-argininal dibutylacetal hydrochloride (0.75 g, 2.3 mmols) in methylene chloride (23 ml) and triethylamine (0.32 ml, 2.3 mmols) were reacted therewith in a manner similar to Example 1 a) to give 0.99 g (75%) of N-benzyloxycarbonyl-L-leucyl-L-argininal dibutylacetal hydrochloride as oil.

TLC: $Rf_1$=0.42–0.52 b) L-Leucyl-L-argininal dibutylacetal hydrochloride

After N-benzyloxycarbonyl-L-leucyl-L-argininal dibutylacetal hydrochloride (0.92 g, 1.60 mmol) was dissolved in methanol (100 ml), palladium black (1 g) was added to the solution. The mixture was stirred at room temperature for 2 hours in a hydrogen flow. After completion of the reaction, the catalyst was filtered off and the filtrate was concentrated to give 0.56 g (80%) of L-leucyl-L-argininal dibutylacetal hydrochloride as oil.

TLC: $Rf_3$=0.43–0.54 c) N-Benzyloxycarbonyl-D-pyroglutamyl-L-leucyl-L-argininal dibutylacetal hydrochloride To a solution of L-leucyl-L-argininal dibutylacetal hydrochloride (0.25 g, 0.57 mmol) in methylene chloride (5.7 ml) were added triethylamine (0.08 ml, 0.57 mmol) and then N-benzyloxycarbonyl-D-pyroglutamic acid-N-hydroxysuccinimide ester (0.23 g, 0.63 mmol) at room temperature. The reaction mixture was stirred overnight at room temperature. After completion of the reaction, the reaction mixture was washed with saturated sodium chloride aqueous solution and concentrated. The residue (0.37 g) was subjected to silica gel column chromatography and eluted with chloroform:methanol:acetic acid (90:10:5) to give 0.23 g (59%) of N-benzyloxycarbonyl-D-pyroglutamyl-L-leucyl-L-argininal dibutylacetal hydrochloride as oil.

TLC: $Rf_1$=0.34–0.41 d) N-Benzyloxycarbonyl-D-pyroglutamyl-L-leucyl-L-argininal hydrochloride

To a solution of N-benzyloxycarbonyl-D-pyroglutamyl-L-leucyl-L-argininal dibutylacetal hydrochloride (0.21 g, 0.30 mmol) in acetonitrile (30 ml) was added 1N hydrochloric acid aqueous solution (15 ml). The mixture was reacted at 36° C. for 2 hours with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 0.14 g (83%) of N-benzyloxycarbonyl-D-pyroglutamyl-L-leucyl-L-argininal hydrochloride.

TLC: $Rf_2$=0.55–0.69 mp=118° C. (dec.)

$[\alpha]_D^{20}$=−13° (c=0.1, DMF)

| Elemental analysis (as $C_{25}H_{37}N_6O_6Cl.2H_2O$) | | | |
|---|---|---|---|
| | C | H | N |
| Calcd. (%) | 50.97 | 7.02 | 14.27 |
| Found (%) | 51.34 | 6.65 | 14.00 |

Example 8

Synthesis of N-benzyloxycarbonyl-D-pyroglutamyl-L-alanyl-L-argininal hydrochloride a) N-Benzyloxycarbonyl-D-pyroglutamyl-L-alanyl-L-argininal dibutylacetal hydrochloride To a solution of L-alanyl-L-argininal dibutylacetal hydrochloride (0.36 g, 0.90 mmol) in methylene chloride (9 ml) were added triethylamine (0.13 ml, 0.90 mmol) and then N-benzyloxycarbonyl-D-pyroglutamic acid-N-hydroxysuccinimide ester (0.36 g, 0.99 mmol) at room temperature. The reaction mixture was stirred overnight at room temperature. After completion of the reaction, the reaction mixture was washed with saturated sodium chloride aqueous solution and concentrated. The residue (0.55 g) was subjected to silica gel column chromatography and eluted with chloroform:methanol:acetic acid (90:10:5, and then 70:10:5) to give 0.29 g (50%) of N-benzyloxycarbonyl-D-pyroglutamyl-L-alanyl-L-argininal dibutylacetal hydrochloride as oil.

TLC: $Rf_1$=0.29–0.35 b) N-Benzyloxycarbonyl-D-pyroglutamyl-L-alanyl-L-argininal hydrochloride

After 1N hydrochloric acid aqueous solution (22 ml) was added to a solution of N-benzyloxycarbonyl-D-pyroglutamyl-L-alanyl-L-argininal dibutylacetal hydrochloride (0.28 g, 0.44 mmol) in acetonitrile (44 ml), the mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 0.19 g (86%) of N-benzyloxycarbonyl-D-pyroglutamyl-L-alanyl-L-argininal hydrochloride.

TLC: $Rf_2$=0.55–0.61 mp=85° C. (dec.)

$[\alpha]_D^{20}$=−16° (c=0.2, DMF)

| Elemental analysis (as $C_{22}H_{31}N_6O_6Cl\ 3/2H_2O.1/5NaCl$) | | | |
|---|---|---|---|
| | C | H | N |
| Calcd. (%) | 48.07 | 6.23 | 15.28 |
| Found (%) | 48.03 | 5.92 | 15.20 |

Example 9

Synthesis of N-benzyloxycarbonyl-D-pyroglutamyl-L-phenylalanyl-L-argininal hydrochloride a) N-Benzyloxycarbonyl-D-pyroglutamyl-L-phenylalanyl-L-argininal dibutylacetal hydrochloride To a solution of L-phenylalanyl-L-argininal dibutylacetal hydrochloride (0.45 g, 0.95 mmol) in methylene chloride (9.5 ml) were added triethylamine (0.13 ml, 0.95 mmol) and then N-benzyloxycarbonyl-D-pyroglutamic acid-N-hydroxysuccinimide ester (0.38 g, 1.05 mmol) at room temperature. The reaction mixture was stirred overnight at room temperature. After completion of the reaction, the reaction mixture was washed with saturated sodium chloride aqueous solution and concentrated. The residue (0.50 g) was subjected to silica gel column chromatography and eluted with chloroform:methanol:acetic acid (110:10:5, and then 80:10:5) to give 0.26 g (39%) of N-benzyloxycarbonyl-D-pyroglutamyl-L-phenylalanyl-L-argininal dibutylacetal hydrochloride as oil.

TLC: $Rf_1$=0.35–0.47 b) N-Benzyloxycarbonyl-D-pyroglutamyl-L-phenylalanyl-L-argininal hydrochloride

After 1N hydrochloric acid aqueous solution (5 ml) was added to a solution of N-benzyloxycarbonyl-D-pyroglutamyl-L-phenylalanyl-L-argininal dibutylacetal hydrochloride (72 mg, 0.10 mmol) in acetonitrile (10 ml), the mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 44 mg (75%) of N-benzyloxycarbonyl-D-pyroglutamyl-L-phenylalanyl-L-argininal hydrochloride.

TLC: $Rf_2$=0.40–0.53 mp=130° C. (dec.)

$[\alpha]_D^{20}$=−46° (c=0.5, DMF)

| Elemental analysis (as $C_{28}H_{35}N_6O_6Cl.3/2H_2O1/3NaCl$) | | | |
|---|---|---|---|
| | C | H | N |
| Calcd. (%) | 53.08 | 6.05 | 13.26 |
| Found (%) | 53.18 | 6.00 | 12.87 |

Example 10

Synthesis of N-benzyloxycarbonyl-D-pyroglutamyl-L-pipecolyl-L-argininal hydrochloride a) N-Benzyloxycarbonyl-D-pyroglutamyl-L-pipecolyl-L-argininal dibutylacetal hydrochloride To a suspension of L-argininal dibutylacetal hydrochloride (0.16 g, 0.50 mmol) in methylene chloride (5 ml) were added triethylamine (0.07 ml, 0.5 mmol) and then N-benzyloxycarbonyl-D-pyroglutamyl-L-pipecolinic acid-N-hydroxysuccinimide ester (0.26 g, 0.55 mmol) at room temperature. The reaction mixture was stirred overnight at room temperature. After completion of the reaction, the reaction mixture was washed with saturated sodium chloride aqueous solution and concentrated. The residue (0.28 g) was subjected to silica gel (14 g) column chromatography and eluted with chloroform:methanol:acetic acid (80:10:5, and then 50:10:5) to give 0.097 g (28%) of N-benzyloxycarbonyl-D-pyroglutamyl-L-pipecolyl-L-argininal dibutylacetal hydrochloride as oil.

TLC: $Rf_1$=0.30–0.36 b) N-Benzyloxycarbonyl-D-pyroglutamyl-L-pipecolyl-L-argininal hydrochloride After 1N hydrochloric acid aqueous solution (3.6 ml) was added to a solution of N-benzyloxycarbonyl-D-pyroglutamyl-L-pipecolyl-L-argininal dibutylacetal hydrochloride (49 mg, 0.072 mmol) in acetonitrile (7 ml), the mixture was reacted at 36° C. for 1.5 hour with stirring. After completion of the reaction, pH of the reaction mixture was adjusted to 4.8 with 1N sodium hydroxide aqueous solution. The solvent was distilled off under reduced pressure and chloroform was added to the residue. Insoluble matters were removed by filtration. After the filtrate was concentrated, the residue was recrystallized from chloroform-hexane to give 27 mg (68%) of N-benzyloxycarbonyl-D-pyroglutamyl-L-pipecolyl-L-argininal hydrochloride.

TLC: $Rf_2$=0.36–0.53

MS: m/z 515 (MH$^+$)

Example 11

Synthesis of L-pyroglutamyl-L-prolyl-L-argininal hydrochloride

After N-benzyloxycarbonyl-L-pyroglutamyl-L-prolyl-L-argininal hydrochloride (0.081 g, 0.15 mmol) was dissolved in dimethlformamide (10 ml), palladium black (1 g) was added to the solution followed by catalytic hydrogenation at room temperature for 30 minutes in a hydrogen flow. After completion of the reaction, the catalyst was filtered off and ether was added to the residue. The precipitated crystals were filtered to give 0.028 g (46%) of L-pyroglutamyl-L-prolyl-L-argininal hydrochloride.

TLC: $Rf_5$=0.34–0.41

| Elemental analysis (as $C_{16}H_{27}N_6O_4Cl.2H_2O$) | | | |
|---|---|---|---|
| | C | H | N |
| Calcd. (%) | 43.78 | 7.12 | 19.15 |
| Found (%) | 43.81 | 7.26 | 19.22 |

Example 12

Synthesis of N-benzyloxycarbonyl-L-pyroglutamyl-L-prolyl-L-argininal ½ sulfate a) N-Benzyloxycarbonyl-L-pyroglutamyl-L-prolyl-L-argininal dibutylacetal ½ sulfate In chloroform was dissolved N-benzyloxycarbonyl-L-pyroglutamyl-L-prolyl-L-argininal dibutylacetal hydrochloride (0.3 g, 0.45 mmol). The solution was washed 3 times with saturated sodium sulfate aqueous solution containing 5% sulfuric acid and twice with 20 ml of saturated sodium sulfate aqueous solution. After drying over magnesium sulfate, the mixture was concentrated and dried under reduced pressure to give N-benzyloxycarbonyl-L-pyroglutamyl-L-prolyl-L-argininal dibutylacetal ½ sulfate as oil.

TLC: $Rf_1$=0.27–0.36

IR (v) cm$^{-1}$: 610, 1120 b) N-Benzyloxycarbonyl-L-pyroglutamyl-L-prolyl-L-argininal ½ sulfate

To a solution of N-benzyloxycarbonyl-L-pyroglutamyl-L-prolyl-L-argininal dibutylacetal ½ sulfate (0.61 g, 0.90 mmol) in acetonitrile (90 ml) was added 1N sulfuric acid aqueous solution (45 ml). The mixture was reacted at 36° C. for 4 hours with stirring. After completion of the reaction, pH of the reaction mixture was adjusted to 5.6 with 1N sodium hydroxide aqueous solution. The solvent was distilled off under reduced pressure and chloroform was added to the residue. Insoluble matters were filtered off. After the filtrate was concentrated, the residue was recrystallized from chloroform-hexane to give 0.43 g (87%) of N-benzyloxycarbonyl-L-pyroglutamyl-L-prolyl-L-argininal. ½ sulfate.

TLC: $Rf_1$=0.13–0.24 mp=90° C. (dec.)

$[\alpha]_D^{20}$=–46° (c=0.5, DMF)

IR (v) cm$^{-1}$: 610, 1110

| Elemental analysis (as $C_{24}H_{33}N_6O_8S_{0.5}.6/5H_2O$) | | | |
|---|---|---|---|
| | C | H | N |
| Calcd. (%) | 50.47 | 6.25 | 14.71 |
| Found (%) | 50.44 | 6.00 | 14.56 |

Example 13

Synthesis of L-pyroglutamyl-L-prolyl-L-argininal ½ sulfate

After N-benzyloxycarbonyl-L-pyroglutamyl-L-prolyl-L-argininal ½ sulfate (0.055 g, 0.10 mmol) was dissolved in 85% methanol (25 ml), a small amount of palladium black (1 g) was added to the solution followed by catalytic hydrogenation at room temperature for an hour in a hydrogen flow. After completion of the reaction, the catalyst was filtered off and the filtrate was concentrated. The residue was dissolved in a small amount of methanol and the solution was poured onto an excess of dry ether. The precipitated crystals were filtered to give 0.032 g (77%) of L-pyroglutamyl-L-prolyl-L-argininal.½ sulfate.

TLC: $Rf_5$=0.20–0.32 mp=180° C. (dec.)

$[\alpha]_D^{20}$=–75° (c=0.25, DMF/H$_2$O (1:1))

IR (v) cm$^{-1}$: 610, 1120

| Elemental analysis (as $C_{16}H_{27}N_6O_6S_{0.5}.2H_2O$) | | | |
|---|---|---|---|
| | C | H | N |
| Calcd. (%) | 42.56 | 6.92 | 18.61 |
| Found (%) | 42.61 | 6.46 | 18.27 |

Example 14

Next, representative test examples are given with regard to the inhibitory activity of some serine proteases for further explanation. The test results are shown in Table 3, by referring to the numbering of the compounds of the present invention in the examples hereinabove. For comparison, known protease inhibitors were used. Their structural formulae are shown in Table 1 and the test results are shown in Table 2.

As synthetic substrates for examining the activity of inhibitor for inhibiting digestion of the substrates with enzyme, there were used PS-994 (H-D-Lys(Tos)-Phe-Lys-CHA.2HCl; manufactured by Nitto Boseki Co., Ltd.) for plasmin, PS-915 (H-D-Phe-Pro-Arg-CHA.2HCl; manufactured by Nitto Boseki Co., Ltd.) for thrombin and trypsin; PS-2000 (Z-D-Lys(HCO)-Gly-Arg-CHA.HCl; manufactured by Nitto Boseki Co., Ltd.) for factor Xa; S-2302 (H-D-Pro-Phe-Arg-pNA; manufactured by Kabi Co., Ltd.) for kallikrein; and

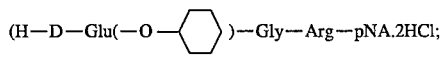

manufactured by Nitto Boseki Co., Ltd.) for urokinase.

As plasmin, thrombin, trypsin, factor Xa, kallikrein and urokinase, there were used 0.3 CU/ml of standard plasmin from Sankyo Color Test $\alpha_2$-PI Measurement Kit, 1.2 NIH U/ml of thrombin from Sankyo Color Test AT-III Measurement Kit, 2 µg/ml of trypsin of Code 3703 of Worthington, 0.25 U/ml of human factor Xa manufactured by Boehringer Mannheim, 0.12 U/ml of human serum kallikrein manufactured by Kabi Co., Ltd. and 1000 U/ml of Urokinase 60000 (60,000 U/vial) manufactured by Mochida Pharmaceutical Co., Ltd., respectively. As a stopping (color forming) solution, there was used the one from the kit of Sankyo Color Test in the case of CHA type substrate. Enzyme reactions were carried out at 37° C.

Inhibitory Activity Against Plasmin

To 0.4 ml of buffer solution (150 mM sodium chloride aqueous solution containing 100 mM Tris, pH 7.8) is added an aqueous solution (0.1 ml) of the inhibitor having various concentrations. The mixture is heated for 5 minutes. After 0.2 ml of plasmin solution is added thereto, the mixture is reacted for 5 minutes. Then 0.1 ml of PS-994 solution (10 mM) is added followed by reaction for 5 minutes. After completion of the reaction, 2.0 ml of the stopping color forming solution is added. After allowing to stand for 10 minutes, absorbance is measured at 700 nm and a concentration of the inhibitor in the reaction system showing absorbance of ½ in the absence of the inhibitor is determined as $IC_{50}$.

Inhibitory Activity Against Thrombin

To 0.4 ml of buffer solution (150 mM sodium chloride aqueous solution containing 150 mM Tris, pH 8.5) is added an aqueous solution (0.1 ml) of the inhibitor having various concentrations. The mixture is heated for 5 minutes. After 0.2 ml of thrombin solution is added thereto, the mixture is reacted for 5 minutes. Then 0.1 ml of PS-915 solution (10 mM) is added followed by reaction for 5 minutes. Thereafter, 2 ml of the stopping color forming solution is added. After allowing to stand for 10 minutes, absorbance is measured at 700 nm and $IC_{50}$ is determined according to the method described above.

Inhibitory Activity Against Trypsin

To 0.5 ml of buffer solution (150 mM sodium chloride aqueous solution containing 150 mM Tris, pH 8.0) is added 0.1 ml of an aqueous solution of the inhibitor. After the mixture is heated for 5 minutes, 0.1 ml of trypin solution is added thereto. Further 0.1 ml of PS-915 solution (10 mM) is added followed by reaction for 5 minutes. Thereafter, 2 ml of the stopping color forming solution [containing 2.5 mg/ml of soybean trypsin inhibitor (manufactured by Sigma Co., No. T-9003)] is added. After allowing to stand for 10 minutes, absorbance is measured at 700 nm and $IC_{50}$ is determined according to the method described above.

Inhibitory Activity Against Factor Xa

To 0.3 ml of buffer solution (150 mM sodium chloride aqueous solution containing 50 mM Tris, pH 8.5) is added 0.1 ml of an aqueous solution of the inhibitor having various concentrations. After the mixture is heated for 5 minutes, 0.1 ml of factor Xa solution (150 mM sodium chloride aqueous solution containing 50 mM Tris and 20 mM calcium chloride, pH 8.5) is added thereto and the mixture is reacted for 5 minutes. Further 5% polyvinylpyrrolidone solution (0.1 ml) containing 10 mM PS-2000 is added followed by reaction for 5 minutes. Thereafter, 2 ml of the stopping color forming solution is added. After allowing to stand for 10 minutes, absorbance is measured at 700 nm and $IC_{50}$ is determined according to the method described above.

Inhibitory Activity Against Kallikrein

To 0.4 ml of buffer solution (150 mM sodium chloride aqueous solution containing 50 mM Tris, pH 8.0) is added 0.1 ml of an aqueous solution of the inhibitor. After the mixture is heated for 5 minutes, 0.1 ml of kallikrein solution (containing 0.5% bovine serum albumin, No. A-8022 manufactured by Sigma Co.) is added thereto followed by reaction for 5 minutes. Further 10 mM S-2302 aqueous solution (0.1 ml) is added thereto. After reacting for 5 minutes, 5 ml of 20% acetic acid aqueous solution is added to terminate the reaction. Absorbance is measured at 405 nm and $IC_{50}$ is determined according to the method described above.

Inhibitory Activity Against Urokinase

To 0.3 ml of buffer solution (150 mM sodium chloride aqueous solution containing 50 mM Tris, pH 8.20) is added 0.1 ml of an aqueous solution of the inhibitor having various concentrations. After the mixture is heated for 5 minutes, 0.1 ml of urokinase solution (150 mM sodium chloride aqueous solution containing 50 mM Tris and 0.1% BSA, pH 8.20) is added thereto and the mixture is reacted for 5 minutes. Then 10 mM MUK-34 aqueous solution (0.1 ml) is added to the mixture. After reacting for 5 minutes, 10% acetic acid aqueous solution (2.0 ml) is added to terminate the reaction. Absorbance is measured at 405 nm and $IC_{50}$ is determined according to the method described above.

TABLE 1

Known Compound

| No. | Compound | Structural Formula |
|---|---|---|
| A1 | Leupeptin | Ac—L—Leu—L—Leu—L—Arg—H·1/2H$_2$SO$_4$ |
| A2 | fPA | H—D—Phe—L—Pro—L—Arg—H·H$_2$SO$_4$ |
| A3 | FOY | 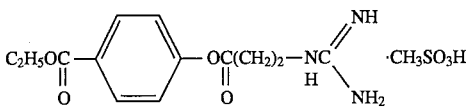 |

TABLE 2

IC$_{50}$ of Known Compound (× 10$^{-7}$)

| Compound No. | Plasmin | Thrombin | Trypsin | Kallikrein | Factor Xa | Urokinase |
|---|---|---|---|---|---|---|
| A1 | 200 | 5900 | 7.8 | 69 | 140 | 10$^3$< |
| A2 | 190 | 0.25 | 0.69 | 310 | 250 | 420 |
| A3 | 400 | 320 | 19 | 45 | 130 | 11 |

TABLE 3

| No. | X | L/D | A$_2$ | Y | Plasmin | Thrombin | Trypsin | Kallikrein | Factor Xa | Urokinase |
|---|---|---|---|---|---|---|---|---|---|---|
| 1  | Z | L | Pro | HCl | 32 | 0.56 | 0.062 | 50 | 3.6 | 220 |
| 2  | Z | L | Ala | HCl | 72 | 59 | 0.074 | 78 | 5.2 | 76 |
| 3  | Z | L | Phe | HCl | 11 | 350 | 0.69 | 4.2 | 5.9 | 760 |
| 6  | Z | D | Pro | HCl | 46 | 220 | 0.62 | 130 | 50 | 11 |
| 7  | Z | D | Leu | HCl | 28 | 10$^3$< | 4.3 | 31 | 47 | 300 |
| 9  | Z | D | Phe | HCl | 13 | 10$^3$< | 10 | 8.7 | 7.2 | 400 |
| 13 | H | L | Pro | ½H$_2$SO$_4$ | 14 | 220 | 0.2 | 55 | 130 | 6.8 |

Leupeptin (acetyl-L-leucyl-L-leucyl-L-argininal) and fPA (D-phenylalanyl-L-prolyl-L-argininal) which are structurally similar to the compounds of the present invention inhibit trypsin and thrombin, respectively but do not strongly inhibit other plasmin, kallikrein, factor Xa and urokinase. Turning to the compounds of the present invention, the compounds are characteristic by strongly inhibiting many trypsin-like serine proteases such as plasmin, thrombin, trypsin, kallikrein, factor Xa and urokinase, as described above. Therefore, the compounds of the present invention can inhibit various trypsin-like serine proteases in vivo and are expected to show remarkable effects as novel protease inhibitors.

What is claimed is:

1. A tripeptide derivative represented by the formula:

X—A$_1$—A$_2$—A$_3$—H wherein X is bound to the secondary amino group of A$_1$ and is selected from the group consisting of a hydrogen atom, an arenesulfonyl group, an alkanesulfonyl group, an aroyl group, an acyl group, and an alkyloxycarbonyl group; A$_1$ is L- or D-pyroglutamic acid; A$_2$ is selected from the group consisting of glycine, L-alanine, L-valine, L-isoleucine, L-serine, L-threonine, L-lysine, L-proline, L-pipecolinic acid and L-phenylalanine; and A$_3$ is an L-, D- or DL-arginal residue or a pharmaceutically acceptable acid addition salt thereof.

2. The tripeptide derivative of claim 1 wherein the arenesulfonyl group is substituted with an alkyl group or an alkyloxy group; the alkanesulfonyl group is substituted with an aryl group; the aroyl group is substituted with an alkyl group, a halogen atom, an amine derivative group or an alkyloxy group; the acyl group is substituted with an aryl group; and the alkyloxycarbonyl group is substituted with an aryl group.

* * * * *